United States Patent
Saito et al.

(10) Patent No.: US 11,927,521 B2
(45) Date of Patent: Mar. 12, 2024

(54) ANALYSIS THRESHOLD DETERMINATION DEVICE AND ANALYSIS THRESHOLD DETERMINATION METHOD

(71) Applicant: JVCKENWOOD Corporation, Yokohama (JP)

(72) Inventors: Atsushi Saito, Yokohama (JP); Shigehiko Iwama, Yokohama (JP); Masahiro Yamamoto, Yokohama (JP)

(73) Assignee: JVCKENWOOD CORPORATION, Yokohama (JP)

( * ) Notice: Subject to any disclaimer, the term of this patent is extended or adjusted under 35 U.S.C. 154(b) by 771 days.

(21) Appl. No.: 17/108,757

(22) Filed: Dec. 1, 2020

(65) Prior Publication Data

US 2021/0080373 A1     Mar. 18, 2021

Related U.S. Application Data (63) Continuation of application No. PCT/JP2019/020063, filed on May 21, 2019.

(30) Foreign Application Priority Data

Jun. 6, 2018    (JP) ................................ 2018-108516

(51) Int. Cl.
*G01N 15/00*     (2006.01)
*G01N 15/14*     (2006.01)
(Continued)

(52) U.S. Cl.
CPC ............ *G01N 15/14* (2013.01); *G01N 21/41* (2013.01); *G01N 33/543* (2013.01); *G01R 23/10* (2013.01); *G01S 7/4873* (2013.01)

(58) Field of Classification Search
USPC ...................................................... 356/5.01
See application file for complete search history.

(56) References Cited

U.S. PATENT DOCUMENTS

| | | | |
|---|---|---|---|
| 2008/0204719 A1* | 8/2008 | Trainer | G01N 15/0205 356/73 |
| 2016/0097837 A1* | 4/2016 | Richley | G01S 5/0244 342/465 |

(Continued)

FOREIGN PATENT DOCUMENTS

| | | | | |
|---|---|---|---|---|
| EP | 2871762 A1 * | 5/2015 | | H02M 3/157 |
| JP | H5-5741 A | 1/1993 | | |

(Continued)

OTHER PUBLICATIONS

International Preliminary Report on Patentability for application PCT/JP2019/020063 (5 pages) (Year: 2020).*

*Primary Examiner* — James R Hulka
(74) *Attorney, Agent, or Firm* — Nath, Goldberg & Meyer; Jerald L. Meyer (57) ABSTRACT

An analysis threshold determination device includes a threshold determination unit for determining a pair of or plural pairs of thresholds used for analysis in accordance with a pair of thresholds generated by a calculation unit and a count value output from a pulse count unit. The calculation unit repeatedly generates a new pair of thresholds in which at least one of the pair of thresholds is changed every time the pulse count unit counts the pulse until reaching a predetermined value. The threshold determination unit chooses a class of a measure of central tendency according to a frequency distribution defining each pair of thresholds generated as a class and the count value output from the pulse count unit as a frequency. The threshold determination unit determines a pair of or plural pairs of thresholds corresponding to a class of a predetermined range from the class of measure of central tendency.

5 Claims, 9 Drawing Sheets

(51) Int. Cl.
*G01N 21/41* (2006.01)
*G01N 33/543* (2006.01)
*G01R 23/10* (2006.01)
*G01S 7/48* (2006.01)
*G01S 7/487* (2006.01)

(56) References Cited

U.S. PATENT DOCUMENTS

| | | | |
|---|---|---|---|
| 2016/0202164 A1* | 7/2016 | Trainer | G01N 15/0211 356/336 |
| 2017/0003213 A1* | 1/2017 | Ono | G01N 33/543 |
| 2017/0010260 A1* | 1/2017 | Ono | G01N 15/1456 |
| 2017/0184582 A1* | 6/2017 | Ono | G01N 33/54373 |

FOREIGN PATENT DOCUMENTS

| | | | |
|---|---|---|---|
| JP | 2002-530786 A | | 9/2002 |
| JP | 2010109195 A | * | 5/2010 |

* cited by examiner

| $V_L$ | COUNT VALUE |
|---|---|
| 0 | Count(0) |
| 1 | Count(1) |
| 2 | Count(2) |
| ⋮ | ⋮ |
| $V_n$ | Count($V_n$) |
| $V_{n+1}$ | Count($V_{n+1}$) |
| ⋮ | ⋮ |
| $V_{max}$ | Count($V_{max}$) |

ANALYSIS THRESHOLD DETERMINATION DEVICE AND ANALYSIS THRESHOLD DETERMINATION METHOD

CROSS REFERENCE TO RELATED APPLICATION

This application is a Continuation of PCT Application No. PCT/JP2019/020063, filed on May 21, 2019, and claims the priority of Japanese Patent Application No. 2018-108516, filed on Jun. 6, 2018, the entire contents of both of which are incorporated herein by reference.

BACKGROUND

The present disclosure relates to an analysis threshold determination device and an analysis threshold determination method. More particularly, the present disclosure relates to an analysis threshold determination device and an analysis threshold determination method for analyzing biomaterials such as antigens and antibodies.

Immunoassays are known that quantitatively analyze disease detection and therapeutic effects by detecting particular antigens or antibodies associated with diseases as biomarkers. One of the immunoassays is an enzyme-linked immunosorbent assay (ELISA) for detecting antigens or antibodies labeled by enzymes, which is widely used because of having the advantage of low costs.

The ELISA requires a long time, such as several hours to a day, for completing an analyzing process including pretreatment, antigen-antibody reaction, bond/free (B/F) separation, and enzyme reaction. To deal with this problem, a technology is disclosed in which antibodies fixed to an optical disc are allowed to bind to antigens in a specimen, and the antigens are further bound to particles provided with antibodies and scanned with an optical head, so as to count the particles captured on the optical disc in a short period of time (refer to Japanese Unexamined Patent Application Publication No. H05-5741). Another technology is disclosed in which biosamples and particles are caused to adhere to a surface of an optical disc having a tracking structure so as to detect a change in signal by an optical pickup (refer to Japanese Translation of PCT International Application Publication No. 2002-530786).

SUMMARY

Since pulses are generated as reflection signals from an optical disc derived from particles adhering to the optical disc, the use of the pulses enables the count of particles.

The particles adhering to the optical disc are quite small and are sometimes in the order of a nanometer-scale. The particles typically cannot have a constant size and thus cause great variation in pulse width and pulse amplitude of the pulses. The particles when including metal, for example, tend to have an influence on the reflection characteristics of light, and cause the variation in pulse width and pulse amplitude of the pulses more significantly.

Since signals of pulses other than the pulses derived from the particles could also be counted upon counting a large number of pulses, a signal-noise (S/N) ratio may be decreased accordingly.

An analysis threshold determination device according to an aspect of the present disclosure includes an optical pickup configured to irradiate an analysis substrate with an irradiation light and receive a reflection light of the irradiation light from the analysis substrate to generate a light reception level signal. The analysis substrate has a surface to which a detection target substance and a particle bound to the detection target substance are fixed. The analysis threshold determination device includes a calculation unit configured to generate a pair of thresholds for a pulse width of a pulse included in the light reception level signal or a pair of thresholds for a pulse amplitude of the pulse. The analysis threshold determination device includes a pulse determination unit configured to determine whether the pulse width is present within a range of the pair of thresholds for the pulse width or determine whether the pulse amplitude is present within a range of the pair of thresholds for the pulse amplitude. The analysis threshold determination device includes a pulse count unit configured to count the pulse determined to be present within the range of the generated pair of thresholds by the pulse determination unit, and output a count value of the pulse counted. The analysis threshold determination device includes a threshold determination unit configured to determine a pair of or plural pairs of thresholds used for analysis in accordance with the pair of thresholds generated by the calculation unit and the count value output from the pulse count unit. The calculation unit repeatedly generates a new pair of thresholds in which at least one of the pair of thresholds is changed every time the pulse count unit counts the pulse until reaching a predetermined value. The threshold determination unit chooses a class of a measure of central tendency according to a frequency distribution defining each pair of thresholds generated as a class and the count value output from the pulse count unit as a frequency. The threshold determination unit determines the pair of or plural pairs of thresholds corresponding to a class of a predetermined range from the class of the measure of central tendency.

An analysis threshold determination method according to an aspect of the present disclosure includes an irradiation step of irradiating, with an irradiation light, an analysis substrate having a surface to which a detection target substance and a particle bound to the detection target substance are fixed. The analysis threshold determination method includes a signal generation step of receiving a reflection light of the irradiation light from the analysis substrate to generate a light reception level signal. The analysis threshold determination method includes a determination step of determining whether a pulse included in the light reception level signal is present within a range of a pair of thresholds set for a pulse width or determining whether the pulse is present within a range of a pair of thresholds set for a pulse amplitude. The analysis threshold determination method includes a count value output step of counting the pulse determined to be present within the range of the set pair of thresholds in the determination step, and outputting a count value of the pulse counted. The analysis threshold determination method includes a threshold generation step of repeatedly generating a new pair of thresholds in which at least one of the pair of thresholds is changed every time the count value output step counts the pulse until reaching a predetermined value. The analysis threshold determination method includes a measure of central tendency choice step of choosing a class of a measure of central tendency according to a frequency distribution defining each pair of thresholds generated as a class and the count value output in the count value output step as a frequency. The analysis threshold determination method includes a threshold determination step of determining a pair of or plural pairs of thresholds corresponding to a class of a predetermined range from the class of the measure of central tendency as a pair of or plural pairs of thresholds used for analysis.

DETAILED DESCRIPTION

An analysis threshold determination device and an analysis threshold determination method according to the present embodiment are described below. The dimensions of the elements in the drawings are exaggerated for illustration purposes, and are not necessarily drawn to scale.

First Embodiment

An analysis threshold determination device and an analysis threshold determination method according to a first embodiment are described in detail below.

Figure 1:
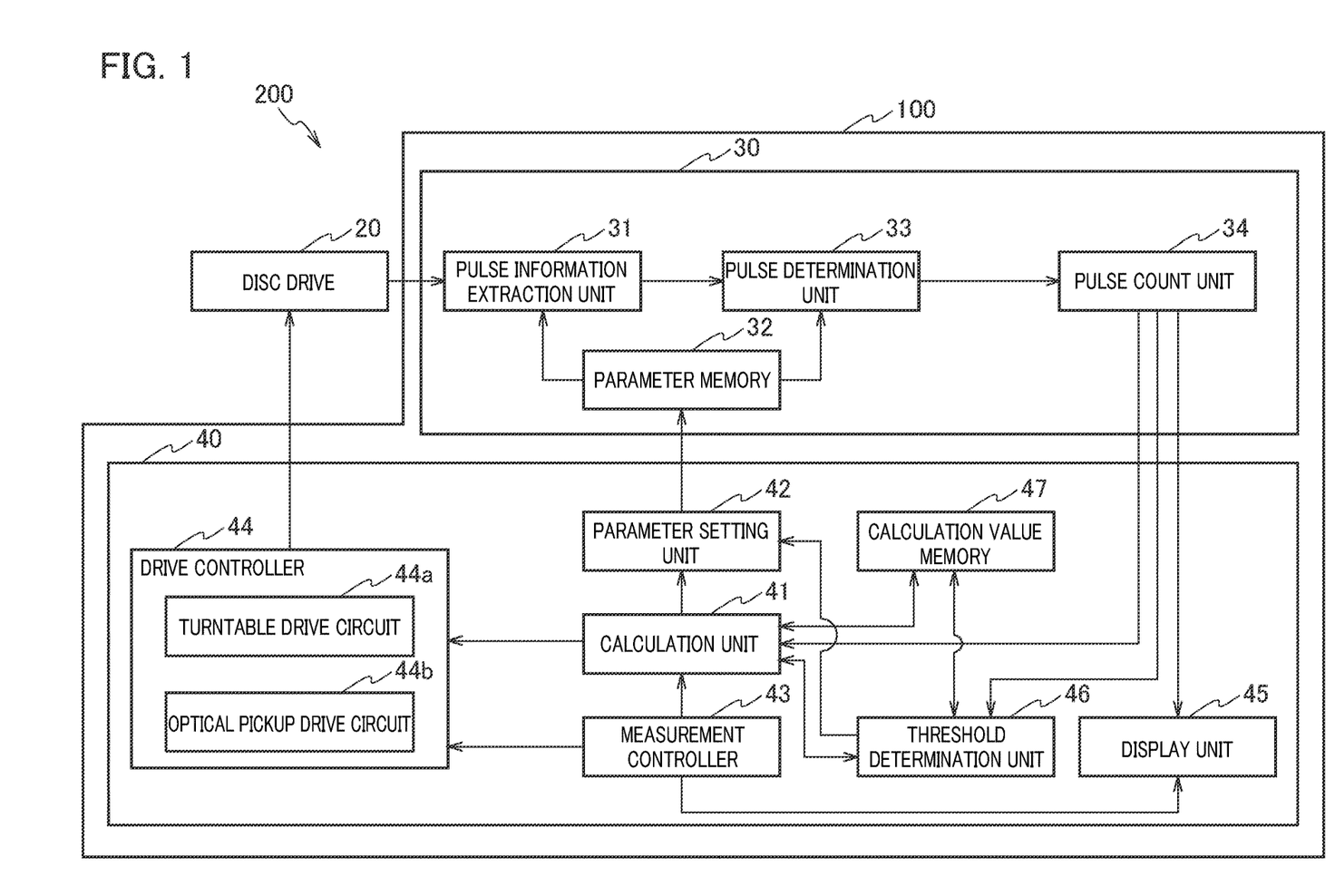
FIG. 1 is a block diagram showing a configuration of an analysis device including an analysis threshold determination device according to a first embodiment.

As shown in FIG. 1, the analysis threshold determination device 100 according to the present embodiment includes a pulse detection circuit 30 and a system controller 40. The present embodiment is illustrated below with an analysis device 200 including the analysis threshold determination device 100 and a disc drive 20.

The disc drive 20 plays an analysis substrate 10. The analysis substrate 10 has a disc-like shape equivalent to optical discs such as Blu-ray discs (BDs), DVDs, and compact discs (CDs). The analysis substrate 10 is formed of resin material, such as polycarbonate resin and cycloolefin polymer, used for common optical discs. The analysis substrate 10 is not limited to the optical discs described above, and may be any optical disc having other configurations or conforming to prescribed standards.

Figure 2:
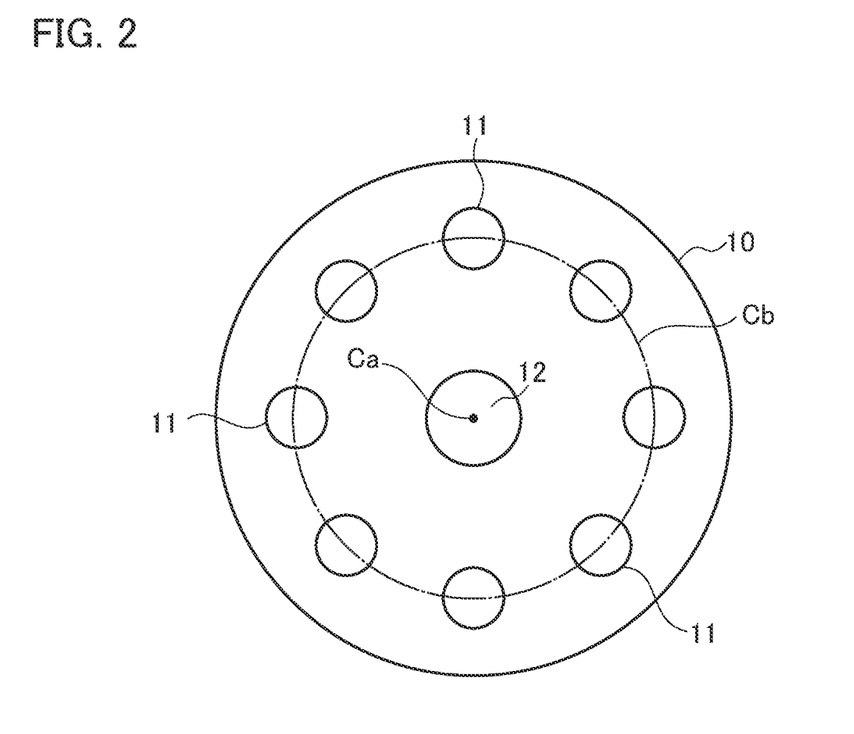
FIG. 2 is a top view showing an example of an analysis substrate having reaction regions.

As shown in FIG. 2, the analysis substrate 10 has reaction regions 11. The reaction regions 11 are regions as a target to be analyzed to which detection target substances 13, particles 14, and antibodies 15 and the like are fixed (refer to FIG. 4). According to the present embodiment, the analysis substrate 10 has a positioning hole 12 in the middle, and the eight reaction regions 11 are arranged at regular intervals such that the respective center points are located on the common circle Cb with respect to the center Ca of the analysis substrate 10. The number or the arrangement positions of the reaction regions 11 are not limited to this illustration.

Figure 3:
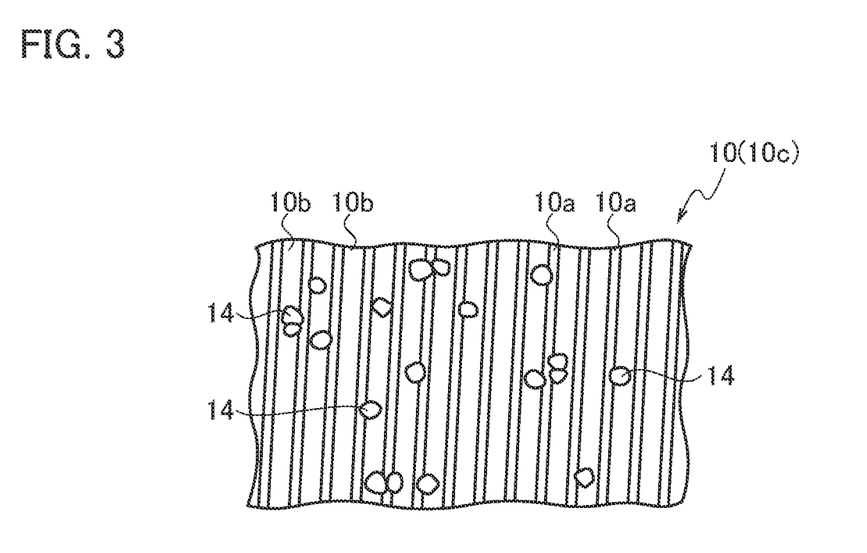
FIG. 3 is an enlarged top view showing a state in which particles are captured on a track region of a reaction region.

As shown in FIG. 3, the surface of the analysis substrate 10 is provided with track regions 10c having convex portions 10a and recesses 10b alternately arranged in a radial direction. The convex portions 10a and the recesses 10b are formed in a spiral from the inner circumference to the outer circumference of the analysis substrate 10. The convex portions 10a correspond to lands of an optical disc. The recesses 10b correspond to grooves of an optical disc. A track pitch of the recesses 10b which is a pitch in the radial direction is 320 nm, for example.

Figure 4:
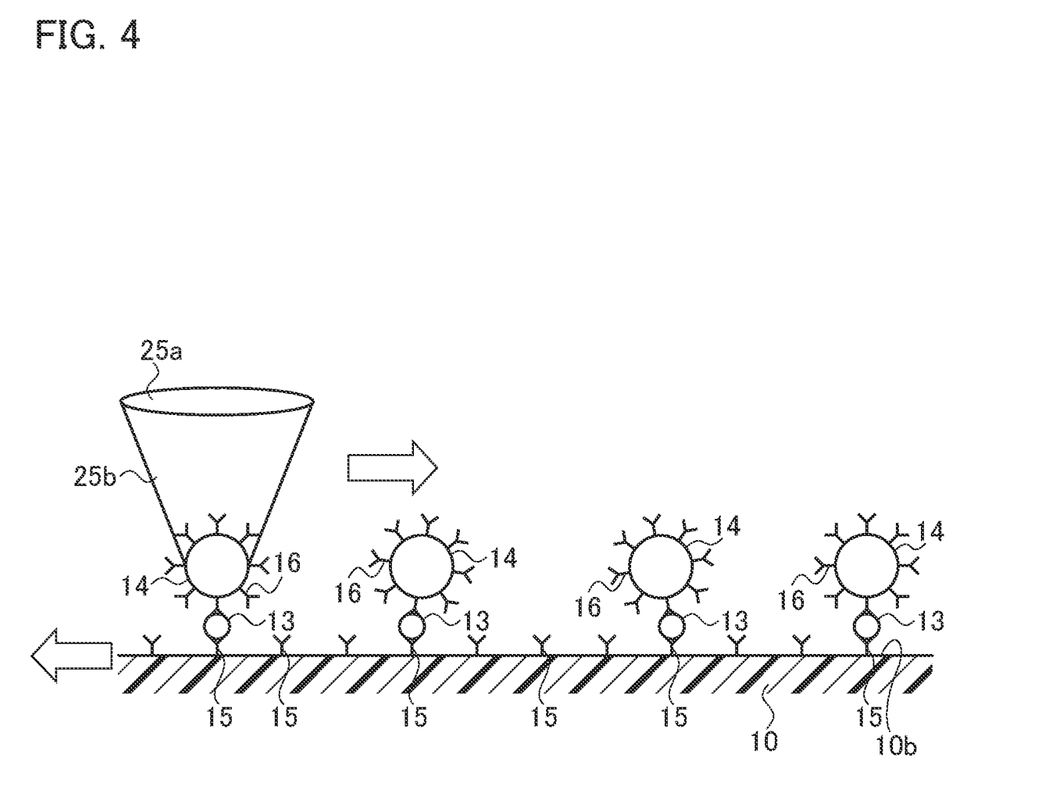
FIG. 4 is a schematic cross-sectional view showing a state in which detection target substances are captured and sandwiched between antibodies and particles in a recess of a track region.

As shown in FIG. 3 and FIG. 4, the detection target substances 13 and the particles 14 bound to the detection target substances 13 are fixed to the surface of the analysis substrate 10. In addition, antibodies 15 specifically binding to the detection target substances 13 are fixed to the surface of the analysis substrate 10. The antibodies 15 recognize and bind to the detection target substances 13 so that the detection target substances 13 are captured on the surface of the analysis substrate 10. The particles 14 are provided with a plurality of antibodies 16 recognizing the detection target substances 13, and are bound to the detection target substances 13 via the antibodies 16 so as to implement a sandwich structure.

The detection target substances 13 are antigens, such as specific protein, associated with diseases, for example. The use of such antigens as the detection target substances 13 contributes to the detection of diseases. For example, the detection target substances 13 such as exosomes vary in concentration in a body fluid depending on a condition of a particular disease as a target to be monitored, so as to serve as biomarkers. The size of the exosomes as the detection target substances 13 is about 100 nm.

The particles 14 serve as labels for the detection target substances 13. Examples of the particles 14 include, but are not limited to, labeling beads such as polymer particles, metallic particles, and silica particles. The particles 14 may be magnetic beads including magnetic material such as ferrite. The size of the particles 14 is about 200 nm.

Figure 5:
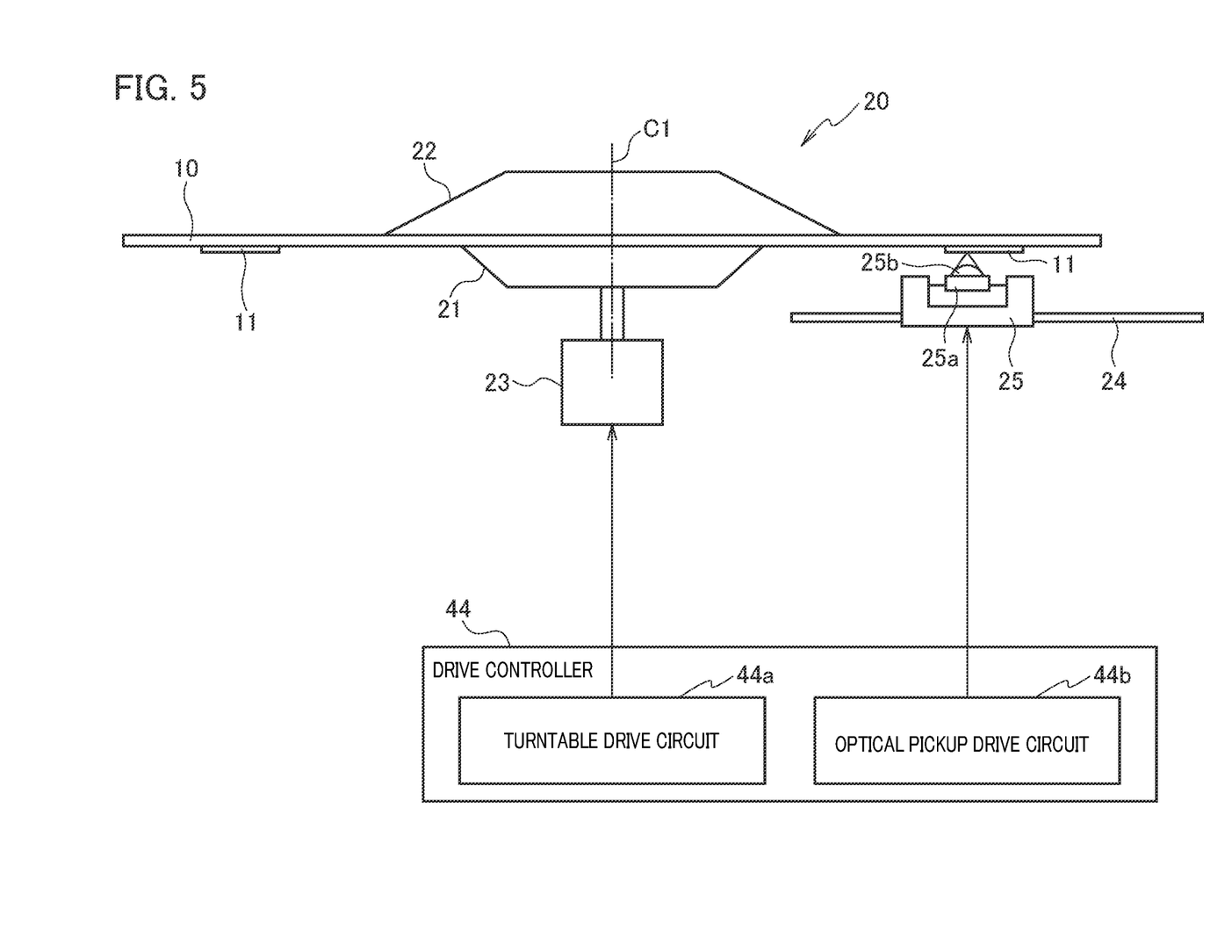
FIG. 5 is a schematic view showing an example of a disc drive according to the present embodiment.

As shown in FIG. 5, the disc drive 20 is an analysis substrate drive device including a turntable 21, a clamper 22, a turntable drive unit 23, a guide shaft 24, and an optical pickup 25. The disc drive 20 may be a known information playing disc drive.

The analysis substrate 10 is placed on the turntable 21 with the surface provided with the reaction regions 11 facing down.

The clamper 22 is driven in directions separating from and approaching the turntable 21, namely, in the upper and lower directions in FIG. 5. The analysis substrate 10 is held on the turntable 21 between the damper 22 and the turntable 21 when the damper 22 is driven in the lower direction. In particular, the analysis substrate 10 is held such that the center Ca of the analysis substrate 10 is located on the rotation axis C1 of the turntable 21.

The turntable drive unit 23 drives the turntable 21 to rotate about the rotation axis C1 together with the analysis substrate 10 and the damper 22. A spindle motor may be used as the turntable drive unit 23. The turntable drive unit 23 is controlled by a turntable drive circuit 44a of a drive controller 44.

The guide shaft 24 is placed in parallel to the analysis substrate 10 in the radial direction of the analysis substrate 10. The guide shaft 24 is arranged in a direction perpendicular to the rotation axis C1 of the turntable 21.

The optical pickup 25 is supported by the guide shaft 24. The optical pickup 25 is driven along the guide shaft 24 in the radial direction of the analysis substrate 10, which is perpendicular to the rotation axis C1 of the turntable 21, and parallel to the analysis substrate 10. The optical pickup 25 is controlled by an optical pickup drive circuit 44b of the drive controller 44.

The optical pickup 25 includes an objective lens 25a. The optical pickup 25 irradiates the analysis substrate 10 with irradiation light 25b. The irradiation light 25b is laser light, for example. The irradiation light 25b is condensed by the objective lens 25a on the surface of the analysis substrate 10. The optical pickup 25 is driven in the radial direction of the analysis substrate 10 which is rotating, so as to scan the recesses 10b with the irradiation light 25b.

The optical pickup 25 receives the reflection light of the irradiation light 25b from the analysis substrate 10 to generate a light reception level signal JS. As shown in FIG. 1, the optical pickup 25 outputs the light reception level signal JS to a pulse information extraction unit 31 of the pulse detection circuit 30.

As shown in FIG. 1, the pulse detection circuit 30 includes the pulse information extraction unit 31, a parameter memory 32, a pulse determination unit 33, and a pulse count unit 34.

The pulse detection circuit 30 acquires the light reception level signal JS output from the disc drive 20, and analyzes a pulse signal derived from the particles 14, so as to acquire count information of the detection target substances 13. The pulse detection circuit 30 is hardware such as a dedicated circuit substrate, for example.

The pulse information extraction unit 31 extracts pulse information from a pulse included in the light reception level signal JS. The pulse information includes a pulse width and a pulse amplitude, for example. The pulse information extraction unit 31 may read out a set value of an extraction parameter stored in the parameter memory 32, and extract the pulse information included in the light reception level signal JS in accordance with the set value of the extraction parameter. For example, when the pulse width is extracted as the pulse information, the pulse information extraction unit 31 may use an extraction voltage $V_{th}$ as the extraction parameter for extracting the pulse width, and extract the pulse width at the extraction voltage $V_{th}$ as the pulse information. When the pulse amplitude is extracted as the pulse information, the pulse information extraction unit 31 may extract a peak value of the pulse as the pulse information. The extracted pulse information is output to the pulse determination unit 33.

The parameter memory 32 stores set values of pulse-related parameters including the extraction parameter and a determination parameter. The determination parameter is used for determining whether the pulse included in the light reception level signal JS is derived from the particles 14. The set value of the determination parameter in the present embodiment is a threshold. Examples of the determination parameter include an amplitude upper-limit voltage $V_H$ which is a threshold voltage of the pulse amplitude on the upper limit side, an amplitude lower-limit voltage $V_L$ which is a threshold voltage of the pulse amplitude on the lower limit side, a pulse width upper-limit time $T_H$ which is a threshold time of the pulse width on the upper limit side, and a pulse width lower-limit time $T_L$ which is a threshold time of the pulse width on the lower limit side.

The pulse determination unit 33 determines whether the pulse included in the light reception level signal JS is present within a range of a pair of thresholds including an upper-limit value and a lower-limit value set in a direction of the pulse width or in a direction of the pulse amplitude. In particular, the pulse determination unit 33 determines whether the pulse width is present within the range of the pair of thresholds regarding the pulse width, or determines whether the pulse amplitude is present within the range of the pair of thresholds regarding the pulse amplitude. The pulse determination unit 33 reads out the set value of the determination parameter from the parameter memory 32, and determines that the pulse is derived from the particles 14 when the pulse information extracted by the pulse information extraction unit 31 is within the range of the set value. As described below, when plural pairs of thresholds chosen by a calculation unit 41 are led out, the pulse determination unit 33 determines whether the pulse included in the light reception level signal JS is present within a range of any one of the plural pairs of thresholds.

The pair of thresholds used for the determination may be set for at least either the pulse width or the pulse amplitude. For example, the pulse determination unit 33 determines that the pulse is derived from the particles 14 when the pulse width at the extraction voltage $V_{th}$ is within the range of the pulse width lower-limit time $T_L$ to the pulse width upper-limit time $T_H$. The pulse determination unit 33 also determines that the pulse is derived from the particles 14 when the pulse amplitude is within the range of the amplitude lower-limit voltage $V_L$ to the amplitude upper-limit voltage $V_H$. The pulse determination unit 33 outputs the detection signal to the pulse count unit 34 so as to increment the count value when the pulse included in the light reception level signal JS is determined to be derived from the particles 14.

The pulse count unit 34 counts the pulse present within the pair of thresholds to output the count value. In particular, the pulse count unit 34 acquires the detection signal in real time to count the pulse derived from the particles 14. The count value is output from the pulse count unit 34 to the calculation unit 41 of the system controller 40, or may be output to a display unit 45 so that a user can recognize the count value. As described below, the calculation unit 41 repeatedly changes at least one of the pair of thresholds by a set amount of change as a unit to generate a new pair of thresholds. The pulse determination unit 33 then counts the pulse determined to be present within the range of each pair of thresholds generated, and outputs the count value of the pulse by the amount of change at a time.

As shown in FIG. 1, the system controller 40 includes the calculation unit 41, a parameter setting unit 42, a measurement controller 43, the drive controller 44, the display unit 45, and a threshold determination unit 46.

The system controller 40 controls the disc drive 20 and the pulse detection circuit 30, and executes the calculation processing and the setting regarding the count value and the determination parameter. The system controller 40 may be a computer on which a software program is installed.

Figure 6:
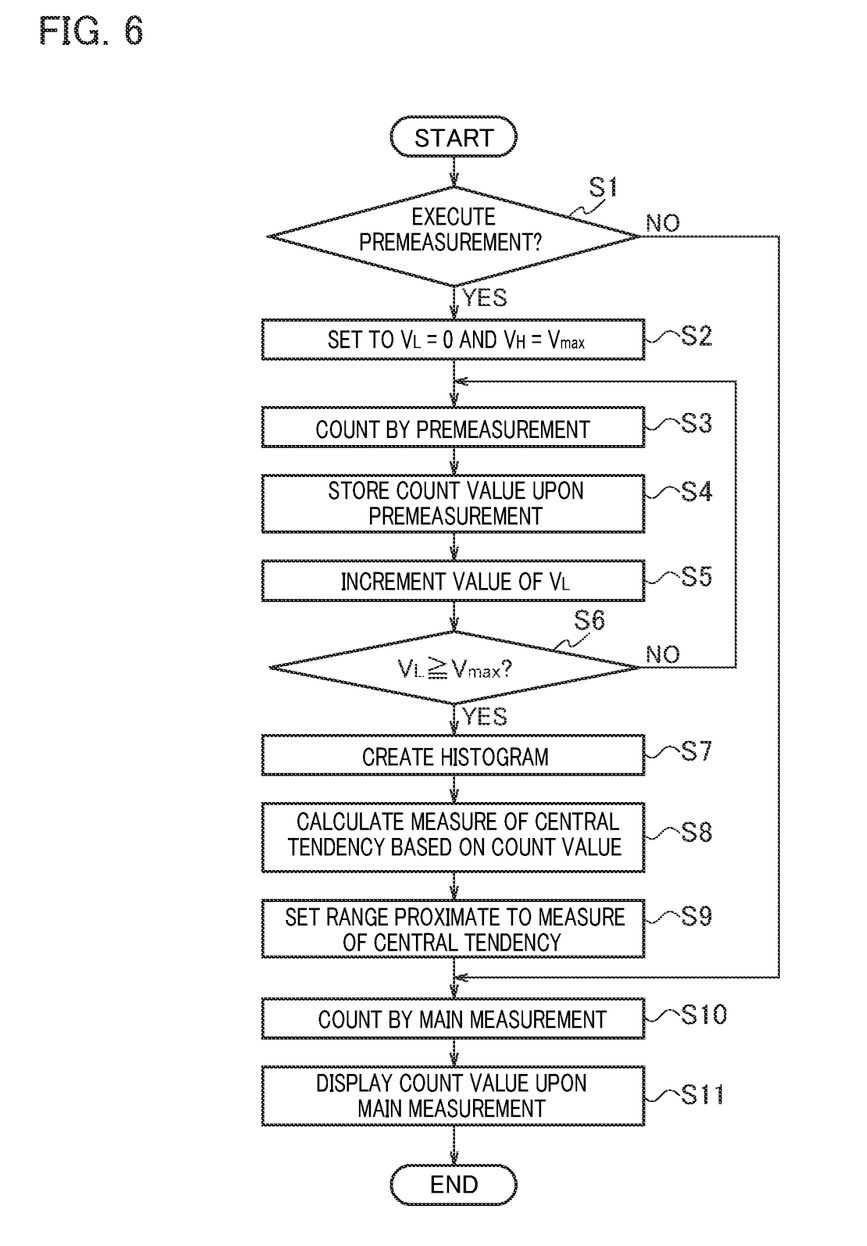
FIG. 6 is a flowchart showing an example of an analysis threshold determination method according to the first embodiment.

The calculation unit 41 executes processing regarding premeasurement and main measurement as shown in the flowchart of FIG. 6 described below. The premeasurement executes the measurement for generating a pair of thresholds according to the intensity of the irradiation light 25b and the state of the reflection characteristics of the analysis substrate 10. The main measurement executes the actual analyzation of the detection target substances 13 with the pair of thresholds generated by the premeasurement.

The calculation unit 41 outputs, to the drive controller 44, a control demand regarding the premeasurement for the movement of the optical pickup 25 and the rotation of the analysis substrate 10.

The calculation unit 41 repeatedly changes at least one of the pair of thresholds by a set amount of change as a unit to generate a new pair of thresholds. In particular, the calculation unit 41 generates a pair of thresholds for the pulse width of the pulse included in the light reception level signal JS, or a pair of thresholds for the pulse amplitude of the pulse. The calculation unit 41 repeatedly generates a new pair of thresholds in which at least one of the pair of thresholds is changed every time the pulse count unit 34 counts the pulse until reaching a predetermined value. For example, the calculation unit 41 may repeatedly change only the upper-limit or lower-limit threshold by the set amount of change as a unit to generate a new pair of thresholds. The calculation unit 41 may repeatedly change the upper-limit and lower-limit thresholds by the set amount of change as a unit to generate a new pair of thresholds, Both the upper-limit and lower-limit thresholds may be changed such that the gap between the upper-limit value and the lower-limit value are kept constant. The amount of change upon changing the upper-limit and lower-limit thresholds is not limited to the constant value, and may be set within a predetermined range or outside the predetermined range, for example. As described above, the pulse count unit 34 counts the pulse determined to be present within the pair of thresholds by the pulse determination unit 33 every time the calculation unit 41 generates the pair of thresholds, and outputs the count value of the pulse by the amount of change at a time.

The threshold determination unit 46 determines a pair of or plural pairs of thresholds used for analysis in accordance with each pair of thresholds generated by the calculation unit 41 and the count value output from the pulse count unit 34. The threshold determination unit 46 chooses a class of a measure of central tendency according to a frequency distribution defining each pair of thresholds generated by the calculation unit 41 as a class and the count value output from the pulse count unit 34 as a frequency. The count value output from the pulse count unit 34 as used herein is the count value of the pulse by the amount of change at a time described above. The frequency distribution may be a histogram.

The measure of central tendency may be at least one value selected from the group consisting of a mean, a median, and a mode. The mode may be obtained by fitting in a normal distribution, for example. The threshold determination unit 46 may choose the measure of central tendency according, to the frequency distribution to store it in a calculation value memory 47 as described below.

The threshold determination unit 46 determines plural pairs of thresholds corresponding to a class of a predetermined range from the class of the measure of central tendency as the plural pairs of thresholds used for analysis. When the measure of central tendency is the mean, the threshold determination unit 46 may calculate a standard deviation (n) of the frequency distribution, and determine, as the plural pairs of thresholds used for analysis, plural pairs of thresholds included in a class of the standard deviation within a predetermined range from the class of the mean. When new plural pairs of thresholds are determined in accordance with the standard deviation, an approximate range may be determined depending on the variation in distribution. The mean may be calculated by a mean calculation unit in the threshold determination unit 46 to store the mean in the calculation value memory 47. The standard deviation may be calculated by a standard deviation calculation unit in the threshold determination unit 46 to store the standard deviation in a memory such as the calculation value memory 47.

The measure of central tendency is the mean, and the predetermined range is preferably within a range of $\pm 1\sigma$ from the mean. In other words, the threshold determination unit 46 preferably determines plural pairs of thresholds included in a class of a range of $\pm 1\sigma$ from the class of the mean as the plural pairs of thresholds chosen in order to improve the S/N ratio. When the frequency distribution is a histogram, the threshold determination unit 46 may determine plural pairs of thresholds used for analysis so that an area of the histogram about the measure of central tendency as a center is a predetermined ratio or smaller of the entire area of the histogram. In view of the improvement in the S/N ratio, the predetermined ratio is preferably 30% or less, and more preferably 10% or less. The thresholds used for analysis are not the plural pairs, and may be a single pair of thresholds.

The calculation value memory 47 stores the measurement values such as the measure of central tendency and the standard deviation chosen in the threshold determination unit 46.

The parameter setting unit 42 receives the output from the calculation unit 41 and stores the value of the parameter to be set in the parameter memory 32.

The measurement controller 43 manages the execution of the premeasurement and the main measurement. The measurement controller 43 may include an input unit for allowing the user to choose the execution of the premeasurement or the main measurement. The measurement controller 43 may direct the drive controller 44 to execute the start, interruption, and completion of the count, or direct the calculation unit 41 and the threshold determination unit 46 to execute the calculation processing, according to the information selected through the input unit.

The drive controller 44 receives the input from the measurement controller 43 to control the disc drive 20. The drive controller 44 can control a measurement position such as a measurement start position and a measurement end position of the analysis substrate 10 in the disc drive 20. The drive controller 44 may include the turntable drive circuit 44a and the optical pickup drive circuit 44b, for example.

The turntable drive circuit 44a controls the turntable drive unit 23. For example, the turntable drive circuit 44a controls the turntable drive unit 23 so as to cause the turntable 21 to rotate together with the analysis substrate 10 and the damper 22 at a constant linear velocity.

The optical pickup drive circuit 44b controls to drive the optical pickup 25. For example, the optical pickup drive circuit 44b moves the optical pickup 25 along the guide shaft 24, or moves the objective lens 25a of the optical pickup 25 in the upper-lower direction.

The drive controller 44 controls the disc drive 20 so as to repeatedly measure the same position even time at least one of the pair of thresholds is changed by the calculation unit 41 during the premeasurement. For example, the drive controller 44 controls the optical pickup 25 so as to move to the measurement start position and the measurement end position, for example. To decrease the time for the premeasurement, the range of the premeasurement is preferably narrower than the range of the main measurement. In particular, the region for counting the pulse present within the range of a new pair of thresholds obtained upon the change made by the calculation unit 41 is preferably narrower than the region for counting the pulse within the pairs of thresholds used for analysis.

The measurement start position and the measurement end position may be preliminarily determined, or may be determined so as to obtain a predetermined count value during the premeasurement. Preliminarily determining the measurement start position and the measurement end position is preferable because the counting is only required to be repeated while at least one of the pair of thresholds is changed, which can simplify the correction. Determining the measurement start position and the measurement end position so as to obtain a predetermined count value during the premeasurement is preferable because the premeasurement can be made with the count value of a predetermined amount or greater, which can achieve a stable premeasurement. In such a case, the measurement start position and the measurement end position of the disc drive 20 are controlled via the calculation unit 41. If the entire measurement target region measured during the main measurement is subjected to the premeasurement, it takes a lot of time. The target for the premeasurement is thus preferably assigned to substantially the middle of the measurement region for the main measurement, which is narrower than the entire measurement target region.

The display unit 45 can provide the user with the information about the premeasurement or the main measurement. An example of the information about the premeasurement is additional information such as an accuracy upon the premeasurement so as to allow the user to choose the subsequent processing. An example of the information about the main measurement is the count value upon the main measurement. The display unit 45 may be any device that can provide the user with the information about the premeasurement or the main measurement, and an example thereof is a display.

The respective steps in the analysis threshold determination method according to the present embodiment are described below with reference to the flowchart shown in FIG. 6. The present embodiment is illustrated below with a system in which a pulse projecting downward is generated when the particles 14 are present in a graph of which the axis of abscissas is a scanning time (a scanning position) and the axis of ordinates is a voltage. In particular, the present embodiment is illustrated with a case in which the amplitude lower-limit voltage $V_L$, the amplitude upper-limit voltage $V_H$, and the extraction voltage $V_{th}$ are each an integer proportional to the voltage within a range of 0 to +100 for illustration purposes. The present embodiment is also illustrated with the system in which a signal level in which no reflection light is detected is set to 100, and a signal level in which no particles 14 or no foreign substances are present on the analysis substrate 10 is set to a reference voltage $V_{base}$ while the signal level is set to a smaller value than the reference voltage $V_{base}$ when the particles 14 are present on the analysis substrate 10. The value of the reference voltage $V_{base}$ depends on the state of the analysis substrate 10 and the intensity of the irradiation light 25b.

The present embodiment, however, is not limited to the system described above. For example, a signal intensity (a voltage value) of the light reception level signal may be directly used, and the amplitude lower-limit voltage $V_L$, the amplitude upper-limit voltage $V_H$, and the extraction voltage $V_{th}$ may each be a decimal. In addition, the present embodiment may employ a system in which the reference voltage $V_{base}$ is zero, and a polarity of the pulse may be inverted so that the pulse projecting upward is generated when the particles 14 are present.

In step S1, the premeasurement is determined whether to be executed. The calculation unit 41 leads the process to proceed to step S2 when the premeasurement is executed (YES), or leads the process to proceed to step S10 when the premeasurement is not executed (NO). The process may proceed to step S10 so as to execute only the main measurement in a case in which the analysis conditions are common, since the premeasurement does not need to be executed each time. The determination of whether the premeasurement is executed may be made by the user through a graphical user interface (GUI), or may be made by the calculation unit 41 according to the information about a usage period or the number of usage times.

In step S2, the calculation unit 41 controls the parameter setting unit 42 so as to set the value of the amplitude lower-limit voltage $V_L$ to zero. The calculation unit 41 also controls the parameter setting unit 42 so as to set the value of the amplitude upper-limit voltage $V_H$ to a value $V_{max}$ which is sufficiently greater than a preliminarily-set initial value $V_{H0}$. When the pulse width upper-limit time $T_H$ and the pulse width lower-limit time 11 are used instead of the amplitude lower-limit voltage $V_L$ and the amplitude upper-limit voltage $V_H$, the calculation unit 41 only needs to control the parameter setting unit 42 so as to set the extraction voltage $V_{th}$ to a preliminarily-set initial value $V_{th0}$. The calculation unit 41 then leads the process to proceed to step S3.

In step S3, the calculation unit 41 controls the drive controller 44 so as to count the particles 14. In particular, the calculation unit 41 controls the drive controller 44 such that the optical pickup 25 is caused to move in the radial direction of the analysis substrate 10 from the measurement start position to the measurement end position for the premeasurement, or such that the analysis substrate 10 is caused to rotate at a regular speed.

The count of the particles 14 is execute by the pulse detection circuit 30. The optical pickup 25 irradiates, with the irradiation light 25b, the surface of the analysis substrate 10 to which the detection target substances 13 and the particles 14 bound to the detection target substances 13 are fixed (an irradiation step). The optical pickup 25 receives the reflection light of the irradiation light 25b from the analysis substrate 10 to generate the light reception level signal JS (a signal generation step). The pulse information of the pulse included in the light reception level signal JS generated is acquired by the pulse information extraction unit 31. The pulse determination unit 33 determines whether the pulse included in the light reception level signal JS is present within the pair of thresholds set for the pulse width, or whether the pulse included in the light reception level signal JS is present within the pair of thresholds set for the pulse amplitude (a first determination step). The pulse determination unit 33 outputs the detection signal to the pulse count unit 34 so as to increment the count value when determining that the pulse included in the light reception level signal JS is present within the pair of thresholds. The pulse count unit 34 counts the pulse present within the pair of thresholds to output the count value to the calculation unit 41. Namely, the pulse count unit 34 counts the pulse determined to be present within the set paired thresholds in the first determination step, and outputs the count value of the pulse counted (a count value output step). The process then proceeds to step S4.

In step S4, the calculation unit 41 stores, in the count table, the count value of the particles 14 acquired upon the premeasurement in step S3 and associated with the value of the set amplitude lower-limit voltage $V_L$. The process then proceeds to step S5.

In step S5, the calculation unit 41 controls the parameter setting unit 42 so as to set again the amplitude lower-limit voltage $V_L$ stored in the parameter memory 32 with the incremented value. For example, when the value of the set amplitude lower-limit voltage $V_L$ is $V_{Ln}$, the calculation unit 41 notifies the parameter setting unit 42 so as to increment the value $V_{Ln}$ to lead the amplitude lower-limit voltage $V_L$ to $V_{Ln+1}$ (n is an integer of zero or greater and smaller than $V_{max}$). While the present embodiment is illustrated with the case in which the calculation unit 41 adds 1 to the original amplitude lower-limit voltage $V_L$, the value to be added is not limited to 1. The calculation unit 41 then leads the process to proceed to step S6.

In step S6, the calculation unit 41 determines whether the set value of the amplitude lower-limit voltage $V_L$ is $V_{max}$ or greater. The calculation unit 41 leads the process to proceed to step S3 when the set value of the amplitude lower-limit voltage $V_L$ is smaller than $V_{max}$ (NO), or leads the process to proceed to step S7 when the set value of the amplitude lower-limit voltage $V_L$ is $V_{max}$ or greater (YES).

Through the process from step S3 to step S6, the calculation unit 41 repeatedly generates a new pair of thresholds in which at least one of the pair of thresholds is changed every time the pulse count unit 34 counts the pulse in the count value output step until reaching a predetermined value (a threshold generation step). In particular, the calculation unit 41 repeatedly adds 1 to the amplitude lower-limit voltage $V_L$ to change the value to a series of different values, namely, new pairs of thresholds, so as to obtain plural values for the amplitude lower-limit voltage $V_L$. When the set value of the amplitude lower-limit voltage $V_L$ is counted from zero to the count table is completed, as shown in FIG. 7, for example.

Figure 7:
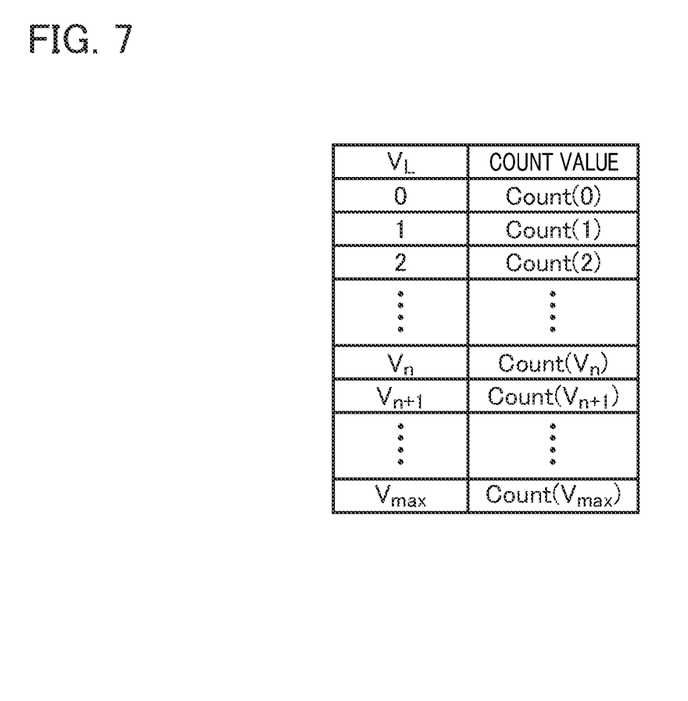
FIG. 7 is a diagram showing an example of a count table according to the present embodiment.

The count table shown in FIG. 7 stores the plural thresholds in the left column, and stores the count values counted for each pair of thresholds changed and obtained. In particular, the count table stores the count value Count ($v_n$) associated with each set value $V_n$ of the amplitude lower-limit voltage $V_L$. The respective count values when set from $V_L=0$ to $V_L=V_{max}$ are stored in the count table as Count (0) to Count ($v_{max}$). The count value Count ($v_n$) is the count value when the set value of the amplitude lower-limit voltage $V_L$ is $V_n$ (n is an integer of zero to $V_{max}$).

In step S7, the pulse count unit 34 counts the pulse determined to be present within each pair of thresholds of the respective paired thresholds by the pulse determination unit 33, and outputs the count value of the pulse by the amount of change at a time. In the present embodiment, the count value of the pulse by the amount of change at a time is given by dCount ($v_n$) according to the following mathematical formula (1):

$$d\text{Count}(v_n) = \text{Count}(v_n) - \text{Count}(v_{n+1}) \quad (1)$$

Figure 8A:
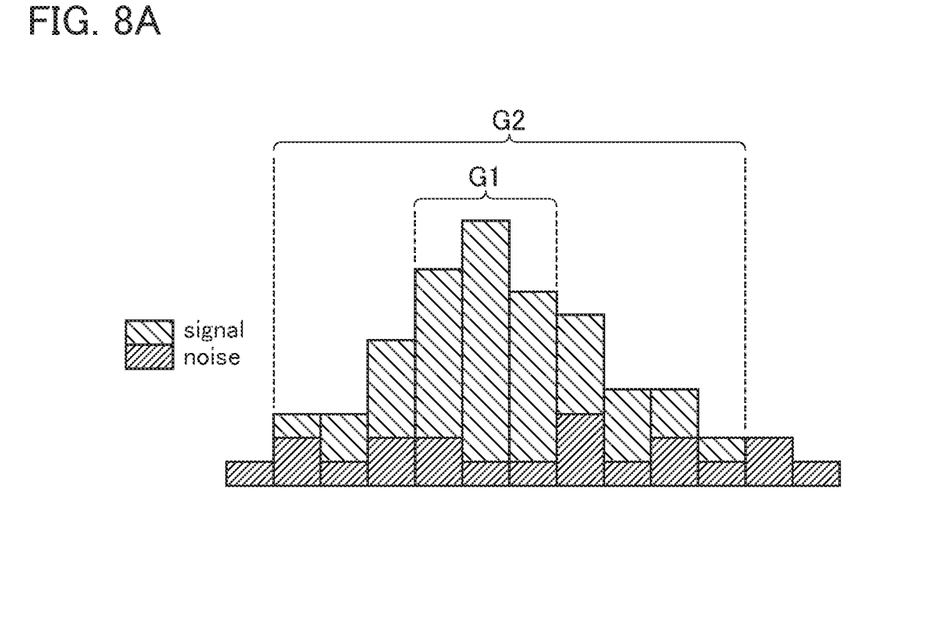
FIG. 8A is a diagram showing an example of a histogram obtained.

The threshold determination unit 46 generates the frequency distribution defining each pair of thresholds as a class and the count value output from the pulse count unit 34 as a frequency. In particular, a histogram as shown in FIG. 8A is obtained in which the amplitude lower-limit voltage $V_L$ is set as a class and dCount ($v_n$) is set as a frequency so as to make a graph from $V_L$=zero to $V_L=V_{max}$. The threshold determination unit 46 then leads the process to proceed to step S8.

In step S8, the threshold determination unit 46 chooses the class of the measure of central tendency according to the frequency distribution defining each pair of thresholds generated in the threshold generation step as a class and the count value output in the count value output step as a frequency (measure of central tendency choice step). The threshold determination unit 46 stores the chosen measure of central tendency in the calculation value memory 47.

Figure 8B:
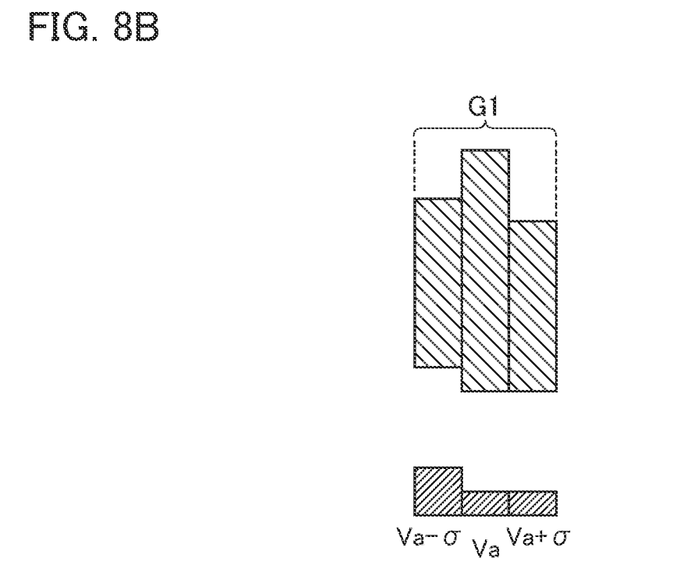
FIG. 8B is a diagram schematically showing a partly extracted graph in region G1 shown in FIG. 8A.

In step S9, the threshold determination unit 46 reads out the measure of central tendency from the calculation value memory 47. The threshold determination unit 46 determines a pair of or plural pairs of thresholds corresponding to a class of a predetermined range from the class of the measure of central tendency as a pair of or plural pairs of thresholds used for analysis (a threshold determination step). FIG. 8B illustrates a case in which the measure of central tendency is the mean, and the thresholds are included within a range of ±1σ from the mean. As shown in FIG. 8B, the threshold determination unit 46 calculates the amplitude lower-limit voltage $V_L$ and the amplitude upper-limit voltage $V_H$ so as to be included within the range of ±1σ about the mean $V_a$ as a center. The amplitude lower-limit voltage $V_L$ and the amplitude upper-limit voltage $V_H$ are calculated according to the following mathematical formula (2) and mathematical formula (3):

$$V_L = V_a - \sigma \quad (2)$$

$$V_H = V_a + \sigma \quad (3)$$

Figure 8C:
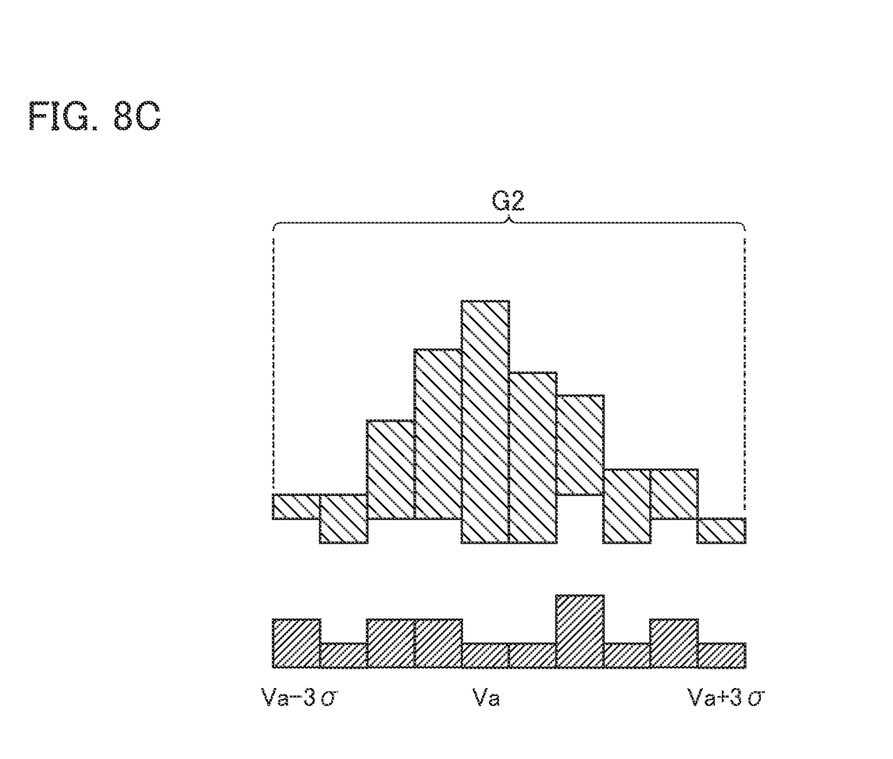
FIG. 8C is a diagram schematically showing a partly extracted graph in region G2 shown in FIG. 8A.

FIG. 8C illustrates a case in which the thresholds are included within a range of ±3σ from the mean. As shown in FIG. 8C, when the thresholds are included within the range of ±3σ from the mean, most of pulses derived from the particles 14 can be counted. The particles 14, when in the order of a nanometer-scale, typically cannot have a constant size. When the particles 14 include metallic material having magnetic properties, the reflection characteristics of the particles 14 vary. It is thus difficult to obtain constant reflection characteristics when the particle diameter of the particles 14 is small. In such a case, pulses derived from noise tend to be counted, as shown in FIG. 8C.

To execute the count processing with a high S/N ratio, the thresholds are preferably included within the range of ±1σ from the mean, as shown in FIG. 8B. The calculation unit 41 then leads the process to proceed to step S10.

In step S10, the calculation unit 41 controls the drive controller 44 so as to count the particles 14 by the main measurement with any one of the pairs of thresholds chosen upon the premeasurement. In particular, the calculation unit 41 controls the drive controller 44 such that the optical pickup 25 is caused to move in the radial direction of the analysis substrate 10 from the measurement start position to the measurement end position for the main measurement, or such that the analysis substrate 10 is caused to rotate at a regular speed.

The drive controller 44 controls the disc drive 20, subjects the analysis substrate 10 to the main measurement from the measurement start position to the measurement end position set for the main measurement, and causes the pulse detection circuit 30 to count the pulse derived from the particles 14. The count of the particles 14 is executed by the pulse detection circuit 30 in the same manner as in step S3, excluding the count with any one of the pairs of thresholds determined upon the premeasurement. The pulse determination unit 33 determines whether the pulse included in the light reception level signal JS is present within the range of any one of the pairs of thresholds determined (a second determination step). The calculation unit 41 then leads to the process to proceed to step S11.

In step S11, the count value upon the main measurement is displayed on the display unit 45, and the main measurement thus ends.

The embodiment has been illustrated above with the case of repeatedly changing one of the pair of thresholds by the set amount of change as a unit, but may repeatedly change both of the pair of thresholds by the set amount of change as a unit. For example, the process may be executed such that the amplitude lower-limit voltage $V_L$ is set to 0 and the amplitude upper-limit voltage $V_H$ is set to 1 in step S2 to increment these voltages to lead $V_L$ to $V_{Ln}+1=V_{Ln+1}$ and lead $V_H$ to $V_{Ln+1}+1=V_{Ln+2}$ in step S5 so as to directly obtain the distribution corresponding to dCount ($v_n$). In this case, the condition for completing the premeasurement in step S6 may be set to be a point at which the set value of $V_H$ is led to $V_{max}$.

The embodiment has been illustrated above with the method of counting the pulse while changing the amplitude lower-limit voltage $V_L$ or the amplitude upper-limit voltage $V_H$ to correct the amplitude lower-limit voltage $V_L$ and the amplitude upper-limit voltage $V_H$. The pulse amplitude and the pulse width are proportional to each other when the pulse waveform is presumed to be a normal distribution. Replacing the amplitude lower-limit voltage $V_L$ with the pulse width lower-limit time $T_L$ and replacing the amplitude upper-limit voltage $V_H$ with the pulse width upper-limit time $T_H$ to execute the same measurement, can also achieve the same effects.

As described above, the analysis threshold determination device 100 according to the present embodiment includes the optical pickup 25 for irradiating the analysis substrate 10 with the irradiation light 25*b* and receiving the reflection light of the irradiation light 25*b* from the analysis substrate 10 so as to generate the light reception level signal JS. The detection target substances 13 and the particles 14 bound to the detection target substances 13 are fixed to the surface of the analysis substrate 10. The analysis threshold determination device 100 includes the calculation unit 41 for generating a pair of thresholds for the pulse width of the pulse included in the light reception level signal JS or a pair of thresholds for the pulse amplitude of the pulse. The analysis threshold determination device 100 includes the pulse determination unit 33 for determining whether the pulse width is present within the range of the pair of thresholds for the pulse width or determining whether the pulse amplitude is present within the range of the pair of thresholds for the pulse amplitude. The analysis threshold determination device 100 includes the pulse count unit 34 for counting the pulse determined to be present within the range of the generated paired thresholds by the pulse determination unit 33, and outputting the count value of the pulse counted. The analysis threshold determination device 100 includes the threshold determination unit 46 for determining a pair of or plural pairs of thresholds used for analysis in accordance with the pair of thresholds generated by the calculation unit 41 and the count value output from the pulse count unit 34. The calculation unit 41 repeatedly generates a new pair of thresholds in which at least one of the pair of thresholds is changed every time the pulse count unit 34 counts the pulse until reaching a predetermined value. The threshold determination unit 46 chooses a class of a measure of central tendency according to the frequency distribution defining each pair of thresholds generated as a class and the count value output from the pulse count unit 34 as a frequency. The threshold determination unit 46 determines the pair of or plural pairs of thresholds corresponding to a class of a predetermined range from the class of the measure of central tendency.

The analysis threshold determination method according to the present embodiment includes an irradiation step of irradiating, with the irradiation light 25*b*, the surface of the analysis substrate 10 to which the detection target substances 13 and the particles 14 bound to the detection target substances 13 are fixed. The analysis threshold determination method includes a signal generation step of receiving the reflection light of the irradiation light 25*b* from the analysis substrate 10 to generate the light reception level signal JS. The analysis threshold determination method includes a determination step of determining whether the pulse included in the light reception level signal JS is present within the range of the pair of thresholds set for the pulse width or determining whether the pulse is present within the range of the pair of thresholds set for the pulse amplitude. The analysis threshold determination method includes a count value output step of counting the pulse determined to be present within the set paired thresholds in the determination step, and outputting the count value of the pulse counted. The analysis threshold determination method includes a threshold generation step of repeatedly generating a new pair of thresholds in which one of the pair of thresholds is changed every time the count value output step counts the pulse until reaching a predetermined value. The analysis threshold determination method includes a measure of central tendency choice step of choosing a class of a measure of central tendency according to the frequency distribution defining each pair of thresholds generated as a class and the count value output in the count value output step as a frequency. The analysis threshold determination method includes a threshold determination step of determining a pair of or plural pairs of thresholds corresponding to a class of a predetermined range from the class of the measure of central tendency as a pair of or plural pairs of thresholds used for analysis.

When any disturbance such as assay noise, scratches on the analysis substrate 10, or the presence of foreign matter is caused, a ratio of noise with respect to the detection target substances 13 tends to increase. The analysis threshold determination device 100 and the analysis threshold determination method according to the present embodiment set the range proximate to the measure of central tendency in the histogram to a new pair of thresholds so as to count only the pulses having pulse amplitudes and pulse widths proximate to the measure of central tendency. The analysis threshold determination device 100 and the analysis threshold determination method thus can reduce the ratio of detection of pulses derived from noise to improve the S/N ratio, as compared with a case of extending a range between the upper limit and the lower limit of thresholds.

Second Embodiment

An analysis threshold determination device 100 and an analysis threshold determination method according to a second embodiment are described in detail below. The same elements as in the first embodiment are denoted by the same reference numerals, and overlapping explanations are not repeated below. The present embodiment is illustrated with a case in which the premeasurement is executed and the measure of central tendency is chosen for each region as a target to be analyzed.

When any disturbance such as assay noise, scratches on the analysis substrate 10, or the presence of foreign matter is caused, the shape of the histogram may vary depending on the measurement region. Choosing the measure of central tendency for each of the measurement regions to execute the main measurement can lead to a count result with a higher S/N ratio for each measurement region.

Figure 9:
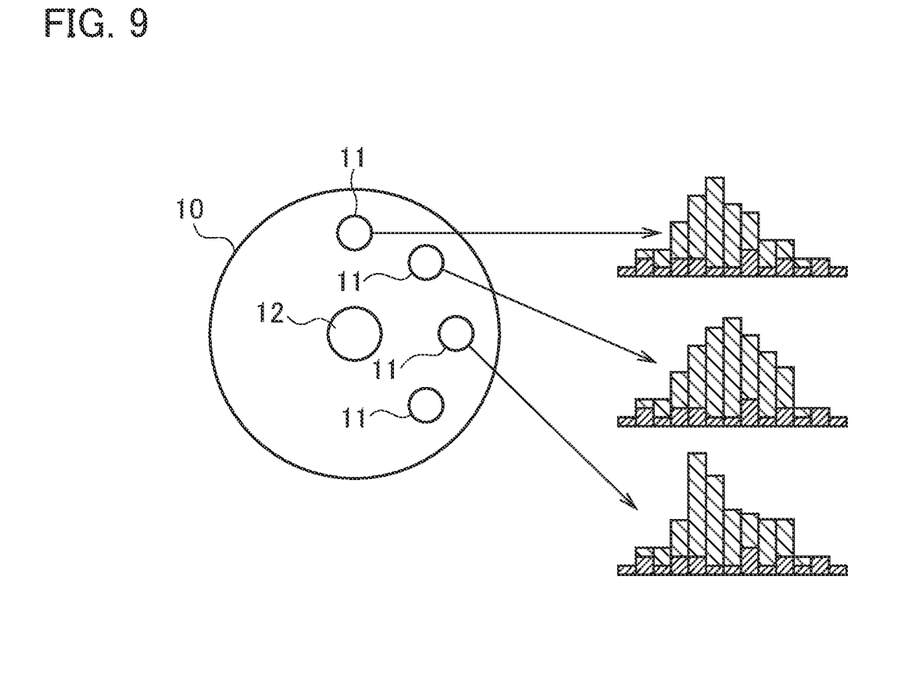
FIG. 9 is a schematic diagram showing a state in which premeasurement is executed for each reaction region.

The analysis substrate 10 according to the present embodiment includes a plurality of analysis target regions with surfaces to which the detection target substances 13 and the particles 14 are fixed. The analysis target regions may be the plural reaction regions 11 provided on the analysis substrate 10 as illustrated in FIG. 2 and FIG. 9. The reaction regions 11 may be formed with wells, for example. The embodiment shown in FIG. 9 is illustrated with a case in which the premeasurement is executed and the measure of central tendency is chosen for each reaction region 11. Namely, the threshold determination unit 46 determines the thresholds for each reaction region 11. The present embodiment determines a new pair of thresholds for each reaction region 11, so as to execute the count processing with a high S/N ratio in each reaction region 11.

Figure 10:
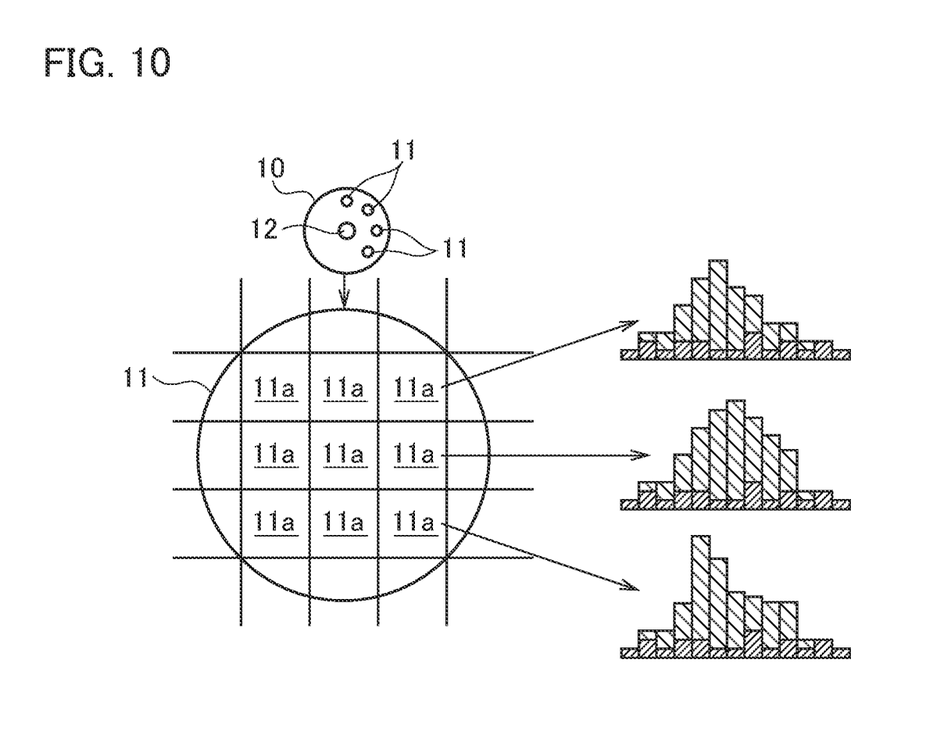
FIG. 10 is a schematic diagram showing a state in which premeasurement is executed for each divided region.

The analysis target regions may be a plurality of divided regions 11*a* obtained such that the respective reaction regions 11 are divided, as illustrated in FIG. 10. The embodiment shown in FIG. 10 is illustrated with a case in which the premeasurement is executed and the measure of central tendency is chosen for each divided region 11*a*. Namely, the threshold determination unit 46 determines the thresholds for each divided region 11*a*. The number of the particles 14 is presumed to vary depending on the spots in the same reaction region 11 in the plane direction of the reaction region 11, which may cause a fluctuation in the optimum value of the measure of central tendency of the pulse width. The present embodiment determines the thresholds for each divided region 11*a*, so as to execute the count processing with a high S/N ratio in each divided region 11*a*. When the measure of central tendency is determined for each divided region 11*a*, a method of specifying the divided region 11*a* to be measured may be determined as appropriate.

Figure 11:
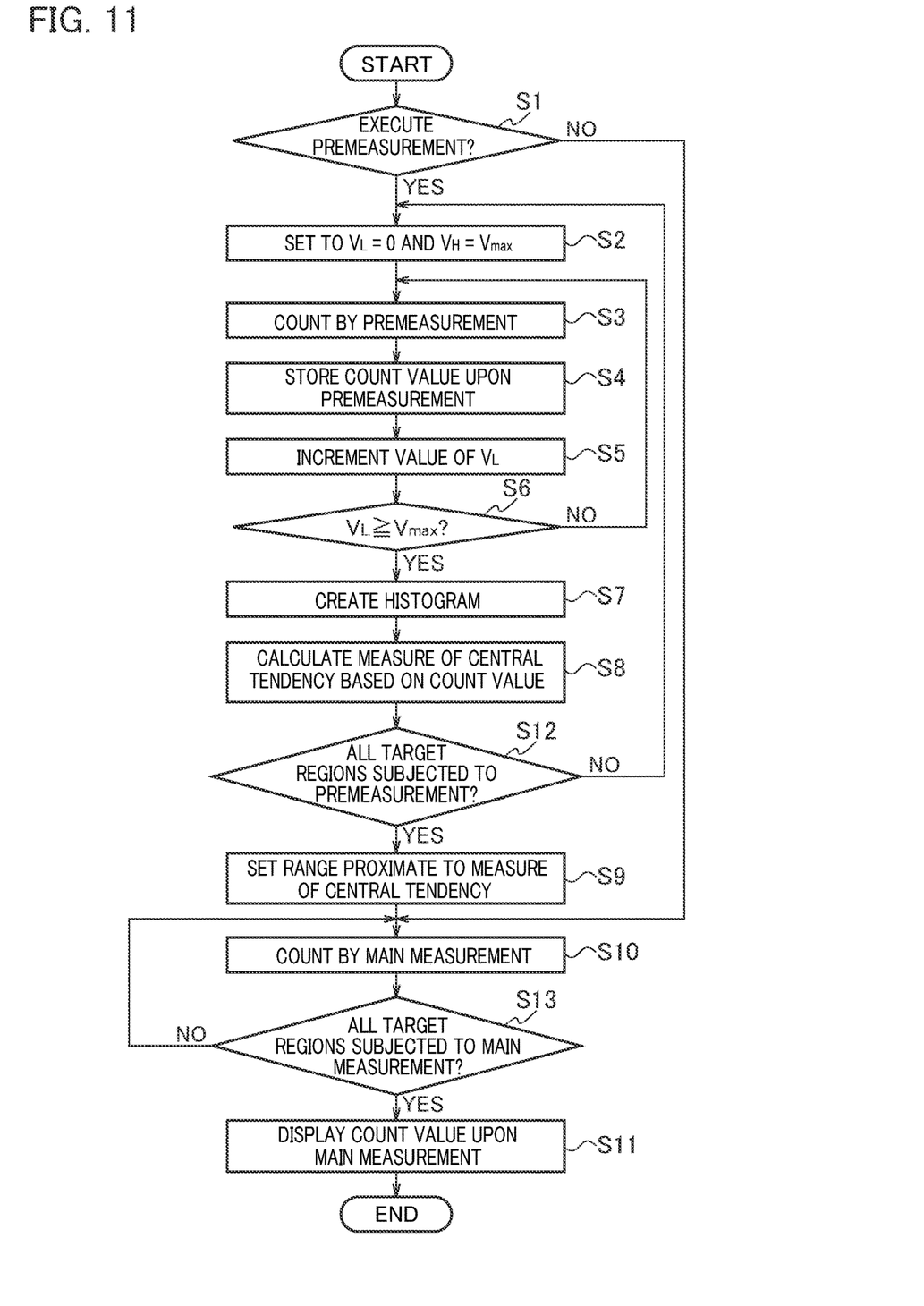
FIG. 11 is a flowchart showing an example of an analysis threshold determination method according to a second embodiment.

The analysis threshold determination device 100 and the analysis threshold determination method according to the present embodiment are described below with reference to the flowchart shown in FIG. 11.

In the process from step S1 to step S8, the threshold determination unit 46 chooses the measure of central tendency of the pulse amplitude and stores it in the calculation value memory 47, as in the case of the first embodiment. The process then proceeds to step S12.

In step S12, the processing is made which determines whether all of the analysis target regions such as the reaction regions 11 are subjected to the premeasurement. For example, when the N-number of the analysis target regions are present, the N-number of the analysis target regions are all determined whether to be subjected to the premeasurement. This determination does not need to be made for all of the N-number of the analysis target regions, and may be made for the analysis regions chosen to be targeted among the N-number of the analysis target regions. When not all of the corresponding analysis target regions are subjected to the premeasurement (NO), the process returns to step S2. When all of the corresponding analysis target regions are subjected to the premeasurement (YES), the process proceeds to step S9.

In the process in step S9 and step S10, the range proximate to the measure of central tendency is set so that the specified regions are counted by the main measurement, as in the case of the first embodiment. The calculation unit 41 then leads the process to proceed to step S13.

In step S13, the calculation unit 41 shifts the measurement target to the subsequent analysis region when the number of the analysis target regions measured is less than the N-number (NO), and returns the process to step S10. The calculation unit 41 leads the process to proceed to step S11 when the number of the analysis target regions measured reaches the N-number (YES), and causes the display unit 45 to display the count value upon the main measurement and controls the measurement controller 43 to end the measurement.

The entire content of Japanese Patent Application No. P2018-108516 (filed on Jun. 6, 2018) is herein incorporated by reference.

While the present embodiments have been described above by reference to the examples, it should be understood that the present embodiments are not intended to be limited to the descriptions above, and various modifications and improvements will be apparent to those skilled in the art.

The present discloser can provide the analysis threshold determination device and the analysis threshold determination method enabling the count processing with a high S/N ratio.

What is claimed is:

1. An analysis threshold determination device comprising:
an optical pickup configured to irradiate, with an irradiation light, an analysis substrate having a surface to which a detection target substance and a particle bound to the detection target substance are fixed, and receive a reflection light of the irradiation light from the analysis substrate to generate a light reception level signal;
a calculation unit configured to generate a pair of thresholds for a pulse width of a pulse included in the light reception level signal or a pair of thresholds for a pulse amplitude of the pulse;
a pulse determination unit configured to determine whether the pulse width is present within a range of the pair of thresholds for the pulse width or determine whether the pulse amplitude is present within a range of the pair of thresholds for the pulse amplitude;
a pulse count unit configured to count the pulse determined to be present within the range of the generated pair of thresholds by the pulse determination unit, and output a count value of the pulse counted; and
a threshold determination unit configured to determine a pair of or plural pairs of thresholds used for analysis in accordance with the pair of thresholds generated by the calculation unit and the count value output from the pulse count unit,
the calculation unit being configured to repeatedly generate a new pair of thresholds in which at least one of the pair of thresholds is changed every time the pulse count unit counts the pulse until reaching a predetermined value,
the threshold determination unit being configured to:
choose a class of a measure of central tendency according to a frequency distribution defining each pair of thresholds generated as a class and the count value output from the pulse count unit as a frequency; and
determine the pair of or plural pairs of thresholds corresponding to a class of a predetermined range from the class of the measure of central tendency.

2. The analysis threshold determination device according to claim 1, wherein the measure of central tendency is at least one value selected from the group consisting of a mean, a median, and a mode.

3. The analysis threshold determination device according to claim 1, wherein the measure of central tendency is a mean, and the predetermined range is within range of ±1σ from the mean.

4. The analysis threshold determination device according to claim 1, wherein:
   the analysis substrate includes a plurality of analysis target regions each having a surface to which the detection target substance and the particle are fixed; and
   the threshold determination unit chooses the measure of central tendency for each of the analysis target regions.

5. An analysis threshold determination method comprising:
   an irradiation step of irradiating, with an irradiation light, an analysis substrate having a surface to which a detection target substance and a particle bound to the detection target substance are fixed;
   a signal generation step of receiving a reflection light of the irradiation light from the analysis substrate to generate a light reception level signal;
   a determination step of determining whether a pulse included in the light reception level signal is present within a range of a pair of thresholds set for a pulse width or determining whether the pulse is present within a range of a pair of thresholds set for a pulse amplitude;
   a count value output step of counting the pulse determined to be present within the range of the set pair of thresholds in the determination step, and outputting a count value of the pulse counted;
   a threshold generation step of repeatedly generating a new pair of thresholds in which at least one of the pair of thresholds is changed every time the count value Output step counts the pulse until reaching a predetermined value;
   a measure of central tendency choice step of choosing a class of a measure of central tendency according to a frequency distribution defining each pair of thresholds generated as a class and the count value output in the count value output step as a frequency; and
   a threshold determination step of determining a pair of or plural pairs of thresholds corresponding to a class of a predetermined range from the class of the measure of central tendency as a pair of or plural pairs of thresholds used for analysis.

* * * * *